(12) United States Patent
Fan et al.

(10) Patent No.: US 7,595,890 B2
(45) Date of Patent: Sep. 29, 2009

(54) POROUS MICROSPHERE RESONATORS (75) Inventors: Xudong Fan, Austin, TX (US); Mark T. Anderson, Woodbury, MN (US); Craig R. Schardt, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 158 days.

(21) Appl. No.: 11/837,604

(22) Filed: Aug. 13, 2007

(65) Prior Publication Data

US 2008/0265147 A1 Oct. 30, 2008

Related U.S. Application Data

(63) Continuation of application No. 10/685,208, filed on Oct. 14, 2003, now Pat. No. 7,259,855.

(51) Int. Cl.
G01B 9/02 (2006.01)

(52) U.S. Cl. .................................. 356/480

(58) Field of Classification Search ............... 356/436, 356/451, 480, 519
See application file for complete search history.

(56) References Cited

U.S. PATENT DOCUMENTS

| 3,833,284 A | 9/1974 | Kaminow et al. |
| 4,715,672 A | 12/1987 | Duguay et al. |
| 4,978,187 A | 12/1990 | Minemura et al. |
| 5,077,822 A | 12/1991 | Cremer |
| 5,091,983 A | 2/1992 | Lukosz |
| 5,214,664 A | 5/1993 | Paoli |
| 5,663,790 A | 9/1997 | Ekström et al. |
| 6,219,361 B1 | 4/2001 | Guch, Jr. et al. |
| 6,389,197 B1 | 5/2002 | Iltchenko et al. |
| 6,490,039 B2 | 12/2002 | Maleki et al. |
| 6,507,684 B2 | 1/2003 | Tapalian et al. |
| 6,512,866 B1 | 1/2003 | Fan et al. |
| 6,583,399 B1 | 6/2003 | Hunziker et al. |
| 6,594,425 B2 | 7/2003 | Tapalian et al. |
| 6,657,731 B2 | 12/2003 | Tapalian et al. |
| 6,665,476 B2 | 12/2003 | Braun et al. |
| 6,668,111 B2 | 12/2003 | Tapalian et al. |

(Continued)

FOREIGN PATENT DOCUMENTS

GB 2 293 883 4/1996

(Continued)

OTHER PUBLICATIONS

Armani, D.K., et al; "Ultra-High-Q Toroid Microcavity on a Chip", Letters to Nature, *Nature* (Feb. 27, 2003); vol. 421, Nature Publishing Group; pp. 925-928.

(Continued)

*Primary Examiner*—Samuel A Turner
(74) *Attorney, Agent, or Firm*—Robert S. Moshrefzadeh (57) ABSTRACT

There are several different applications where it is desirable to increase the amount of material that can be introduced to the surface of a microresonator that has whispering gallery modes. The use of a porous surface on the microresonator permits greater amounts of the material to be captured on or near the surface of the microresonator, resulting in an increased optical interaction between the material and the light propagating in the whispering gallery mode(s) of the microresonator.

15 Claims, 4 Drawing Sheets

U.S. PATENT DOCUMENTS

| | | | |
|---|---|---|---|
| 6,777,244 | B2 | 8/2004 | Pepper et al. |
| 6,781,696 | B1 | 8/2004 | Rosenberger et al. |
| 6,795,481 | B2 | 9/2004 | Maleki et al. |
| 6,813,285 | B2 | 11/2004 | Peterson |
| 6,853,479 | B1 | 2/2005 | Ilchenko et al. |
| 6,865,317 | B2 | 3/2005 | Vahala et al. |
| 6,879,752 | B1 | 4/2005 | Ilchenko et al. |
| 6,888,973 | B2 | 5/2005 | Kolodziejski et al. |
| 6,888,987 | B2 | 5/2005 | Sercel et al. |
| 6,891,996 | B2 | 5/2005 | Sercel et al. |
| 6,891,997 | B2 | 5/2005 | Sercel et al. |
| 6,895,135 | B2 | 5/2005 | Kaneko et al. |
| 6,901,101 | B2 | 5/2005 | Frick |
| 7,019,847 | B1 * | 3/2006 | Bearman et al. ............ 356/480 |
| 7,065,276 | B2 | 6/2006 | Scheuer et al. |
| 7,091,049 | B2 | 8/2006 | Boga et al. |
| 7,095,010 | B2 * | 8/2006 | Scherer et al. ................ 385/12 |
| 7,197,196 | B2 | 3/2007 | Lin et al. |
| 7,245,801 | B2 | 7/2007 | Boyd et al. |
| 7,283,707 | B1 | 10/2007 | Maleki et al. |
| 7,343,067 | B2 | 3/2008 | Barwicz et al. |
| 2001/0038651 | A1 | 11/2001 | Maleki et al. |
| 2002/0018611 | A1 | 2/2002 | Maleki et al. |
| 2002/0041730 | A1 | 4/2002 | Sercel et al. |
| 2002/0044739 | A1 | 4/2002 | Vahala et al. |
| 2002/0068018 | A1 | 6/2002 | Pepper et al. |
| 2002/0079453 | A1 | 6/2002 | Tapalian et al. |
| 2002/0094150 | A1 | 7/2002 | Lim et al. |
| 2002/0097401 | A1 | 7/2002 | Maleki et al. |
| 2002/0172457 | A1 | 11/2002 | Tapalian et al. |
| 2002/0192680 | A1 | 12/2002 | Chan et al. |
| 2003/0016907 | A1 | 1/2003 | LoCascio et al. |
| 2003/0082237 | A1 | 5/2003 | Cha et al. |
| 2004/0023396 | A1 | 2/2004 | Boyd et al. |
| 2004/0091212 | A1 | 5/2004 | Strecker et al. |
| 2004/0120638 | A1 | 6/2004 | Frick |
| 2004/0146431 | A1 | 7/2004 | Scherer et al. |
| 2004/0196465 | A1 | 10/2004 | Arnold et al. |
| 2005/0035278 | A1 | 2/2005 | Margalit et al. |
| 2005/0053319 | A1 | 3/2005 | Doan |
| 2005/0074200 | A1 | 4/2005 | Savchenkov et al. |
| 2005/0077513 | A1 | 4/2005 | Fan et al. |
| 2005/0078731 | A1 | 4/2005 | Fan et al. |
| 2005/0105868 | A1 | 5/2005 | Arakida |
| 2005/0111309 | A1 | 5/2005 | Peng |
| 2005/0147372 | A1 | 7/2005 | Bourdelais et al. |
| 2005/0169582 | A1 | 8/2005 | Tan et al. |
| 2005/0249509 | A1 | 11/2005 | Nagarajan et al. |
| 2005/0263679 | A1 | 12/2005 | Fan et al. |
| 2005/0265658 | A1 | 12/2005 | Fan et al. |
| 2006/0110100 | A1 | 5/2006 | Blauvelt et al. |
| 2006/0159392 | A1 | 7/2006 | Popovic |
| 2006/0170931 | A1 | 8/2006 | Guo et al. |
| 2007/0036500 | A1 | 2/2007 | Suzuki et al. |
| 2007/0071386 | A1 | 3/2007 | Digonnet et al. |
| 2007/0237478 | A1 | 10/2007 | D'Aguanno et al. |
| 2008/0008423 | A1 | 1/2008 | Scheuer et al. |

FOREIGN PATENT DOCUMENTS

| | | |
|---|---|---|
| GB | 2 387 130 | 10/2003 |
| WO | WO 01/40757 | 6/2001 |
| WO | WO 01/67565 | 9/2001 |
| WO | WO 01/85341 | 11/2001 |
| WO | WO 02/13337 | 2/2002 |
| WO | WO 02/16986 | 2/2002 |
| WO | WO 2004/038370 | 5/2004 |

OTHER PUBLICATIONS

Blair et al., "Resonant-enhanced evanescent-wave fluoresence biosensing with cylindrical optical cavities", Applied Optics, vol. 40, No. 4, Feb. 1, 2001, pp. 570-582.

Boyd et al., "Sensitive disk resonator photonic biosensor", Applied Optics, vol. 40, No. 31, Nov. 1, 2001, pp. 5742-5747.

Burlak, G., et al; "Electromagnetic Oscillations in a Multilayer Spherical Stack", *Optics Communications* (Jun. 1, 2000); vol. 180; pp. 49-58.

Burlak, G., et al; "Electromagnetic Eigenoscillations and Fields in a Dielectric Microsphere with Multilayer Spherical Stack", *Optics Communications* (Jan. 1, 2001); vol. 187; pp. 91-105.

Burlak, G., et al; "Transmittance and Resonance Tunneling of the Optical Fields in the Microspherical Metal-Dielectric Structures", *Optics Communications* (2002); vol. 206; pp. 27-37.

Chan, S., et al. "Porous Silicon Microcavities for Biosensing Applications," *Physical Status Solid*, vol. 182, (2000) pp. 541-546.

Chan, S., et al; "Nanoscale Silicon Microcavities for Biosensing" *Materials Science & Engineering C* (2001); vol. 15; pp. 277-282.

Chan, S., et al; "Identification of Gram Negative Bacteria Using Nanoscale Silicon Microcavities", *Journal of American Chemical Society* (2001); vol. 123; pp. 11797-11798.

Coffer et al., "Strategies Toward the Development of Integrated Chemical Sensors Fabricated from Light Emitting Porous Silicon", Proceedings of the SPIE, vol. 3226, 1997, pp. 168-179.

Crisan et al., "Sol-Gel Preparation of Thin Films for Integrated Optics", $10^{th}$ International Symposium on Electron Devices for Microwave and Optoelectronic Applications, 18-19., Nov. 2002, Manchester, UK., pp. 205-210.

De Stefano, L., et al., "Optical Sensing of Flammable Substances Using Porous Silicon Microcavities," *Materials Science and Engineering*, vol. 100, Jul. 25, 2006, pp. 271-274.

Garmire, E. et al, "Propagation Losses in Metal-film-substrate Optical Waveguides". *Journal of Quantum Electronics*, vol. QE-8, No. 10, Oct. 1972, pp. 763-766.

Johnson, B.R.; "Theory of Morphology-Dependent Resonances: Shape Resonances and Width Formulas", *Journal Optical Society of America A* (Feb. 1993); vol. 10, No. 2; pp. 343-352.

Kakarantzas, G., et al; "Miniature All-Fiber Devices Based on $CO_2$ Laser Microstructuring of Tapered Fibers", *Optics Letters* (Aug. 1, 2001); vol. 26, No. 15; pp. 1137-1139.

Kaminow, I.P., et al., "Metal-Clad Optical Waveguides: Analytical and Experimental Study", *Applied Optics*, vol. 13, (1974), pp. 396-405.

Knight, J.C., et al; "Mapping Whispering-Gallery Modes in Microspheres with a Near-Field Probe", *Optics Letters* (Jul. 15, 1995); vol. 20, No. 14; pp. 1515-1517.

Krioukov, E., et al; "Integrated Optical Microcavities for Enhanced Evanescent-Wave Spectroscopy", *Optics Letters* (Sep. 1, 2002); vol. 27, No. 17; pp. 1504-1506.

Krioukov et al., "Sensor based on an integrated optical microcavity", Optics Letters, vol. 27, No. 7, Apr. 1, 2002, pp. 512-514.

Laine, J.-P., et al; "Acceleration Sensor Based on High-Q Optical Microsphere Resonator and Pedestal Antiresonant Reflecting Waveguide Coupler", *Sensors and Actuators A* (2001); vol. 93; pp. 1-7.

Laine, J.-P., et al; "Microsphere Resonator Mode Characterization by Pedestal Anti-Resonant Reflecting Waveguide Coupler", *IEEE Photonics Technology Letters* (Aug. 2000); vol. 12, No. 8; pp. 1004-1006.

Little, B.E., et al; "Pedestal Antiresonant Reflecting Waveguides for Robust Coupling to Microsphere Resonators and for Microphotonic Circuits", *Optics Letters* (Jan. 1, 2000); vol. 25, No. 1; pp. 73-75.

Luk, J.M.C., et al; "Rapid and Sensitive Detection of *Salmonella* (O: 6,7) by Immunomagnetic Monoclonal Antibody-Based Assays", *Journal of Immunological Methods* (1991); vol. 137; pp. 1-8.

Lugo, J.E., et al; "Porous Silicon Multilayer Structures: A Photonic Band Gap Analysis", *Journal of Applied Physics* (Apr. 15, 2002); vol. 91, No. 8, pp. 4966-4972.

Martin, A.L., et al; "Replica-Molded High-Q Polymer Microresonators", *Optics Letters* (Mar. 15, 2004); vol. 29, No. 6; pp. 533-535.

Mulloni, V., et al. "Porous Silicon Microcavities as Optical Chemical Sensors," *Applied Physics Letters*, vol. 76, No. 18, May 1, 2000, pp. 2523-2525.

Otto, A., et al, "Modification of the Total Reflection Modes in a Dielectric Film by One Metal Boundary", *Optics Communications*, vol. 3, No. 4, Jun. 1971, pp. 254-258.

Pettipher, G.L., et al; "Rapid Enumeration of Microorganisms in Foods by the Direct Epifluorescent Filter Technique", *Applied and Environmental Microbiology* (Oct. 1982); vol. 44, No. 4; pp. 809-813.

Pipino et al., "Evanescent wave cavity ring-down spectroscopy with a total-internal-reflection minicavity", Review of Scientific Instruments, American Institute of Physics, vol. 68, No. 8, Aug. 8, 1997, pp. 2978-2989.

Plowman, T. E., et al; "Femtomolar Sensitivity Using a Channel-Etched Thin Film Waveguide Fluoroimmunosensor", *Biosensors & Bioelectronics* (1996); Elsevier Science Ltd.; vol. 11, No. 1/2; pp. 149-160.

Popescu, A., et al; "The Gram Stain after More than a Century", *Biotechnic and Histochemistry* (1996); vol. 71, No. 3; pp. 145-151.

Reisinger, A. "Attenuation Properties of Optical Waveguides with a Metal Boundary", *Appl. Phys. Lett.*, vol. 23, No. 5, Sep. 1, 1973, pp. 237-239.

Shibata et al., "Laser Emission from Dye-Doped Organic-Inorganic Particles of Mircocavity Structure", Journal of Sol-Gel Science and Technology, vol. 8, 1997, pp. 959-964.

Spillane, S.M., et al; "Ultralow-Threshold Raman Laser Using a Spherical Dielectric Microcavity", *Nature* (Feb. 7, 2002); vol. 415; pp. 621-623.

Suematsu, et al, "Fundamental Transverse Electric Field (TE0) Mode Selection for Thin-film Asymmetric Light Guides", *Appl. Phys. Lett.*, vol. 21, No. 6, Sep. 15, 1972, pp. 291-293.

Sumetsky, M., "Whispering-Gallery-Bottle Microcavities: the Three-Dimensional Etalon", *Optics Letters* (Jan. 1, 2004); vol. 29, No. 1; pp. 8-10.

Tapalian, C., et al; "High-Q Silica Microsphere Optical Resonator Sensors Using Stripline-Pedestal Anti-Resonant Reflecting Optical Waveguide Couplers"; *Proceedings from SPIE, Photonics West 2003* (Jan. 25-31, 2003); vol. 4969; Laser Resonators and Beam Control VI; Item 4969-30; pp. 11-22.

Tien, P, et al, "Novel Metal-clad Optical Components and Method of Isolating High-index Substrates for Forming Integrated Optical Circuits", *Appl. Phys. Lett.*, vol. 27, No. 4, Aug. 15, 1975, pp. 251-253.

Tortorello, M.L., et al; "Antibody-Direct Epifluorescent Filter Technique for Rapid, Direct Enumeration of *Escherichia coli* O157:H7 in Beef", *Applied and Environmental Microbioology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Vernooy, D.W., et al; "High-Q Measurements of Fused-Silica Microspheres in the Near Infrared", *Optics Letters* (Feb. 15, 1998); vol. 23, No. 4; pp. 247-249.

Vollmer, F., et al; "Protein Detection by Optical Shift of a Resonant Microcavity", *Applied Physics Letters* (May 27, 2002); vol. 80, No. 21; pp. 4057-4059.

Yoneyama et al., "Nonradiative Dielectric Waveguide Circuit Components", *International Journal of Infrared and Millimeter Waves*, vol. 4, No. 3 (1963), p. 439-449.

Yunfeng et al., "Chemical sensors based on hydrophobic porous sol-gel films and ATR-FTIR spectroscopy", Sensors and Actuator B, Elsevier Sequoia S.A., vol. B36, No. 1, 2, and 3, Oct. 1996, pp. 517-521.

Xu, G.; "Gram Stain", University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.htm>; pp. 10.

* cited by examiner

POROUS MICROSPHERE RESONATORS

CROSS REFERENCE TO RELATED APPLICATIONS

This application is a continuation of U.S. Ser. No. 10/685,208, filed Oct. 14, 2003, now U.S. Pat. No. 7,259,855 now allowed, the disclosure of which is incorporated by reference in its entirety herein.

FIELD OF THE INVENTION

The present invention is directed generally to optical devices, and more particularly to optical devices based on microresonators.

BACKGROUND

Dielectric microspheres or planar waveguide ring- or disk-shaped resonators have attracted increasing attention in sensing applications, including biosensing. The size of these types of resonators typically ranges from approximately 20 μm to a few millimeters for microspheres and from 5 μm to a few tens of microns for ring- or disk-shaped resonators. Such microspheres and ring- or disk-shaped resonators are often referred to as microresonators. In the most common configuration in microresonator-based biosensors, a microresonator is placed in a close proximity to an optical waveguide such as optical fiber whose geometry has been specifically tailored, for example tapered or etched to a size of 1-5 μm.

The tapering modifications to the waveguide result in there being a substantial optical field outside the waveguide, and thus light can couple into the microresonator and excite its eigenmodes, often referred to as whispering gallery modes (WGMs). When microresonators made with low loss materials and with high surface quality are used, the propagation loss of light propagating in WGMs is very low, and extremely high quality factors, also known as Q-factors, can be achieved: values as high as 109 are achievable. Due to the high Q-factor, the light can circulate inside the microsphere resonator for a very long time, thus leading to a very large field enhancement in the cavity mode, and a very long effective light path. This makes such devices useful for non-linear optical and sensing applications. In sensing applications, the samples to be sensed are placed on the sphere's surface, where they interact with the evanescent portion of the WGM available outside the microresonator. Due to the enhanced field and the increased interaction length between the light and samples, the microresonator-based optical sensors feature high sensitivity and/or a low detection limit.

SUMMARY OF THE INVENTION

There exist different applications where it is desirable to increase the amount of material that is to be introduced to the surface of a microresonator. The use of a porous surface permits greater amounts of the material to be captured on or near the surface of the microresonator, resulting in an increased optical interaction between the material and the light propagating within the microresonator. Accordingly, part of the invention is directed to the inclusion of a porous material at least on the surface of the microresonator.

One such application is where the microresonator is used in a sensor to detect an analyte. Despite the high sensitivity associated with microresonator-based sensors, there remains a need to further increase the sensitivity of such devices, thus lowering the detection limit. The high sensitivity of microsphere resonators lies, in part, in the large effective interaction area between the light in WGMs and the samples on the sphere surface, as discussed in the previous section. The use of a porous surface permits more of the analyte to take part in the optical interaction with the light propagating within the microresonator. One particular embodiment of the invention is directed to a microresonator device that comprises a light source to produce light and a first waveguide coupled to receive the light from the light source. At least one microresonator is disposed to couple light into the microsphere from the first waveguide. The microresonator defines whispering gallery modes and has at least a porous surface region.

Another embodiment of the invention is directed to a method of detecting an analyte. The method includes passing light into a first waveguide and coupling light from the first waveguide into a microresonator having a porous surface region. The porous coupling region is covered with a fluid containing the analyte. Light from the microresonator is monitored and the presence of the analyte is determined from the monitored light.

Another embodiment of the invention is directed to a microresonator that has a body operative as a microresonator, defining whispering gallery modes at least a first wavelength. At least an outer portion of the body is porous.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is applicable to optical devices that use microresonators, such as microspheres and micro-planar ring- or disk-shaped resonators for active and/or passive applications. The invention is believed to be particularly useful for using such microresonators in sensing applications where the material to be sensed is placed on or near the surface of the microresonator.

Figure 1A:
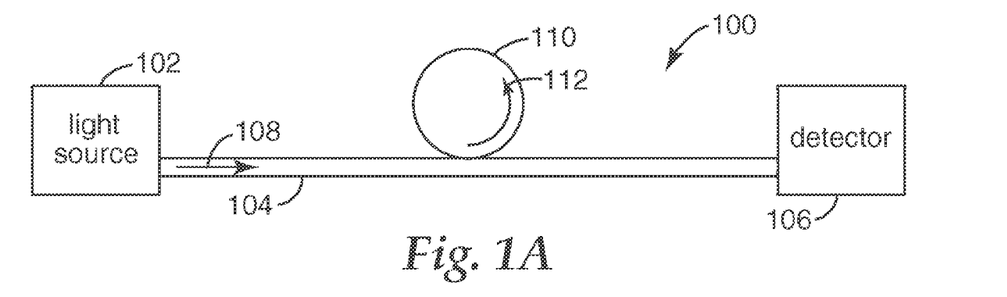
FIGS. 1A and 1B schematically illustrate embodiments of a microresonator-based device.

An exemplary system 100 that uses a microresonator is schematically illustrated in FIG. 1A. This particular system 100 may be used in a sensor device. A light source 102 directs light along a waveguide 104 to a detector unit 106. The microresonator 110 is optically coupled to the waveguide 104. Light 108 from the light source 102 is launched into the waveguide 104 and propagates towards the detector unit 106. The microresonator 110 evanescently couples some of the light 108 out of the waveguide 104. The out-coupled light 112 propagates within the microresonator 110 at one of the resonant frequencies of the microresonator 110.

The light source 102 may be any suitable type of light source. For increased efficiency and sensitivity, it is advantageous that the light source produces light that is efficiently coupled into the waveguide 104, for example a laser such as a laser diode. The light source 104 generates light 108 at a wavelength that interacts with the species being sensed. The light source 104 may be tunable and may or may not generate light 108 in a single longitudinal mode.

The light source 102 may direct light into a number of different waveguides, of which the waveguide 104 is one. The waveguide 104 may be any suitable type of waveguide and may be, for example, a planar or channel waveguide formed in or on a substrate, such as a waveguide formed in a silica substrate. The waveguide 104 may also be an optical fiber.

The detector unit 106 includes a light detector, for example a photodiode or phototransistor, to detect light. The detector unit may also include a wavelength selective device that determines the wavelength of light reaching the light detector. The wavelength selective device may be, for example, a filter, or a spectrometer. The wavelength selective device, for example a spectrometer, may be tunable so as to permit the user to actively change the wavelength of light incident on the light detector.

The microresonator 110 is positioned in contact with, or very close to, the waveguide 104 so that a portion of the light 106 propagating along the waveguide 104 is evanescently coupled into the microresonator 110. The waveguide 104 typically has no cladding, or very thin cladding, at the point where the microresonator 110 couples to the waveguide 104, so that the microresonator 110 couples directly to the waveguide core.

Figure 1B:
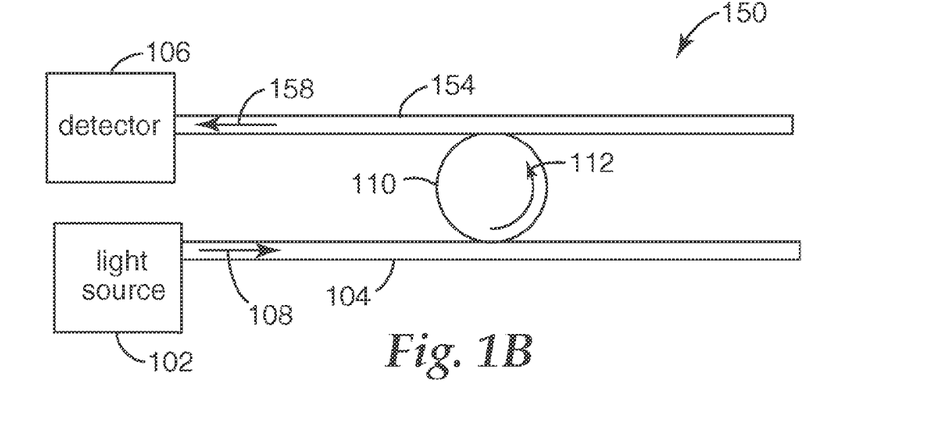

Another type of microresonator device 150 is schematically illustrated in FIG. 1B. In this device 150, light 158 from the microresonator 110 is coupled into a second waveguide 154, and propagates to the detector 106. In this configuration, the detector 106 does not detect light from the light source 102 directly.

Figure 2:
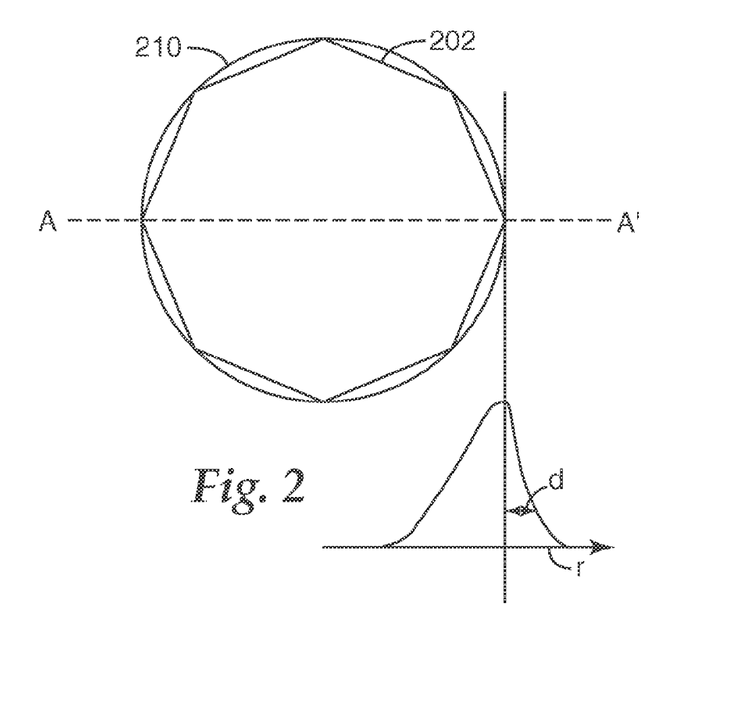
FIG. 2 schematically illustrates electric field distribution for light propagating within a microresonator.

Light propagates within the microresonator 110 in so-called "whispering gallery modes", an example of which is schematically illustrated in FIG. 2. In a whispering gallery mode (WGM) 202, the light propagates around the microresonator 210 from an origin via a number of total internal reflections, until it returns to the origin. In the illustrated embodiment, the WGM 202 includes eight total internal reflections in a single round trip. It will be appreciated that the light may propagate within the microresonator 210 in other WGMs that correspond to different numbers of total internal reflections.

Furthermore, the WGM of the microresonator 210 is a high Q mode for light whose wavelength is equal to an integral fraction of the round trip length of the whispering gallery mode. Stated another way, the whispering gallery mode only demonstrates a high Q where the light is of such a wavelength that it constructively interferes after one round trip. This resonant condition can be stated mathematically as:

$$\lambda_m = L/m \tag{1}$$

where $\lambda_m$ is the wavelength of the mth mode, L is the optical length of one round trip of the WGM, and m is an integer, referred to as the mode number. The microresonator efficiently couples in light from the waveguide 104 that satisfies the resonant condition (1).

The amplitude of the WGM, where the WGM is incident with the side of the microresonator 210, peaks at the interior surface of the microresonator 210. The amplitude of the WGM decays exponentially outside the microresonator 210, with an exponential decay factor, d, given by $d \approx \lambda/n$ where $\lambda$ is the wavelength of the light and n is the refractive index of the medium outside the microresonator 210. The field amplitude is schematically illustrated in FIG. 2 for the WGM 202 along the cross-section line AA'.

Samples of analyte that are to be sensed are introduced to the surface of the microresonator. In one method, at least the porous region of the microresonator's surface, or optionally the entire microresonator, is exposed to a fluid containing the analyte. For example, the fluid may be a liquid containing the analyte in solution or suspension, or may be a gaseous mixture containing the analyte. The light-matter interaction between the WGM and the analyte on the surface of the microresonator is achieved through evanescent coupling.

As the light-matter interaction is proportional to the strength of the local electric field of the WGM, one way to enhance sensitivity is to have samples experience the maximum electric field and hence achieve the maximum interaction with the WGM. In addition, the refractive index change between the interior and exterior of the microresonator depends on the surface adsorption area and the sample molecular weight. A larger interaction area is desirable, particularly for the detection of small molecular weight molecules that form monolayers or only very thin layers.

According to the present invention, the microresonator is formed using porous material at least at the surface of the microresonator. For example, the microresonator may be formed wholly out of porous material or may be formed from a central core of non-porous material, with a coating of porous material surrounding the non-porous core. In either case, the size of pore of the porous material should advantageously be less than the wavelength of the probe light so as to avoid any significant impact on the Q-factor.

Figure 3:
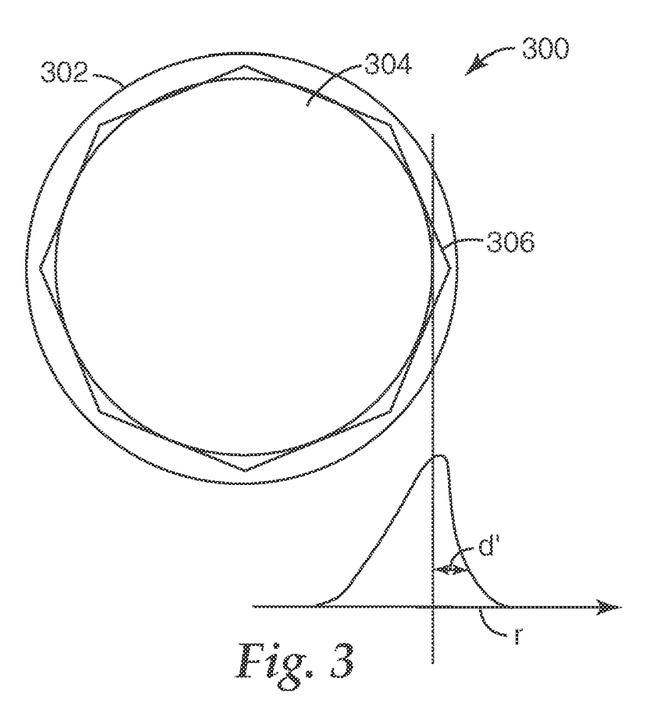
FIG. 3 schematically illustrates electric field distribution for light propagating within an embodiment of a microresonator according to principles of the present invention.

One particular embodiment of a layered type of porous microresonator 300 is schematically illustrated in FIG. 3, having a porous layer 302 over a core 304. The core 304 may be formed of a non-porous material or may be a hollow core. The electric field of the WGM is pulled toward the porous layer 302, compared to the case where the porous layer 302 is replaced with air (or solution such as water). Therefore, the electric field has a larger portion in the porous layer 302, as illustrated in FIG. 3, where sensing occurs, enabling the analytes to be exposed to higher levels of electric field, thus increasing the interaction between the light and the analytes. Furthermore, the use of the porous layer 302 enables the analyte to be denser in the region of the WGM 306, further increasing the light-analyte interaction. The density of the analyte depends, at least in part, on the surface area of the microresonator: an increased surface area results in more sites to which the analyte may become attached, since the analyte tends to form a monolayer over the microresonator. Use of a porous surface results in an increase in the surface area. In an example, the surface area of non-porous particles is in the region of around 1 m² per gram of material (1 m²/g). The surface area of a porous material may be in the range of 1000 m²/g or more. Where the porous material is a layer of porous material about a core, the thickness of the porous layer may be less than $\lambda$, where $\lambda$ is the wavelength of light being used to excite the WGMs of the microresonator. The thickness of the porous layer may also be less than $\lambda/10$.

Figure 4:
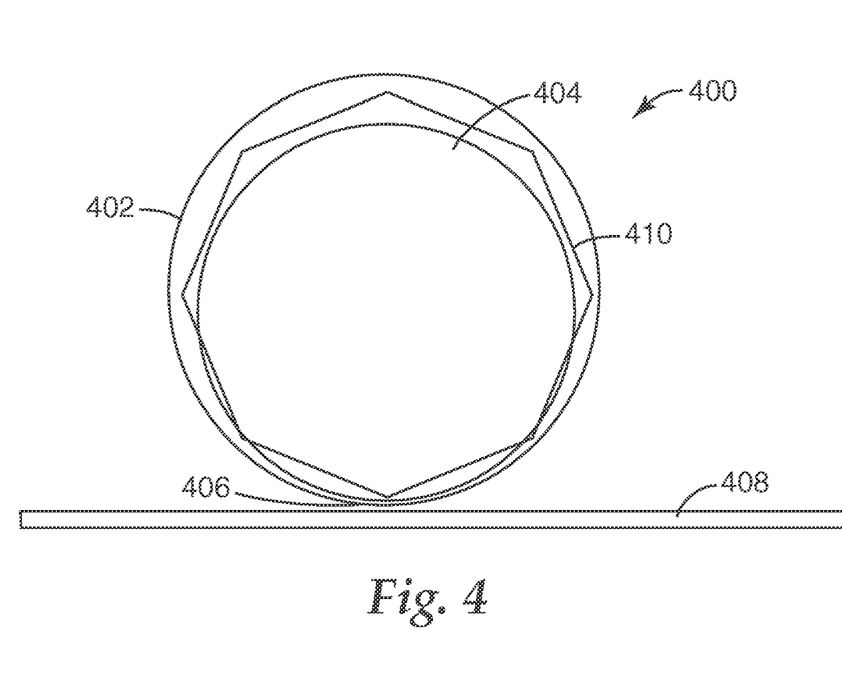
FIG. 4 schematically illustrates another embodiment of a microresonator according to principles of the present invention.

A variation of the layered microresonator 400 design is schematically illustrated in FIG. 4. In this embodiment, the thickness of the porous layer 402 is not constant all the way around the core 404. One of the advantages of this embodiment is that, when the portion 406 of the porous layer 402 that is thinnest is placed close to a waveguide 408, scattering losses that occur when coupling light between the WGMs 410 and the waveguide 408 are reduced. Light coupled into the WGMs 410 is then adiabatically transferred to the porous layer 402 for sensing.

The porous surface of the microresonator may be modified to attract a desired analyte. Once the desired analyte has been attracted to the porous surface, or close to the porous surface, the spectral properties of the microresonator may be changed. For example, the surface of the microresonator may be treated to attract a protein, a DNA molecule, a virus, or a bacterium. In an example of a microresonator prepared to attract a protein, the surface of the microresonator may be initially treated with either an antibody or an antigen, so that the other of the antibody and antigen is attracted to the microresonator when placed into an analyte solution. The antigen may be expressed on the cell wall of a bacterium, in which case the bacterium may be attracted to the microresonator.

In an example of a microresonator prepared to attract a DNA molecule, the microresonator may initially be treated by having a specific DNA strand immobilized on its porous surface. The DNA strand immobilized on the surface of the microresonator is highly selective and only combines with its complementary strand (cDNA). A viral biosensor may have a complementary DNA segment attached to its porous surface. The segment is complementary to a portion of a, typically larger, viral DNA molecule. The cDNA segment is preferably sufficiently long that it binds strongly to the viral DNA molecule. The presence of the viral DNA molecule can then be determined optically. The use of DNA with microresonators is described further in S. Chan et al., "Nanoscale silicon microcavities for biosensing", *Materials Science and Engineering* C 15, pp. 277-282 (2001), incorporated herein by reference.

Any suitable type of material may be used for the microresonator. In an approach in which the microresonator includes a porous layer over a core, the core may be any suitable type of glass, for example: silica glass; modified silicate glass, such as alkali silicate glass; heavy metal oxide glass; halide glass, such as fluoride glass; oxyhalide glass; chalcogenide glass; and phosphate glass. In addition, the core may also be hollow, and need not be completely solid. Therefore, the core may be a hollow body, for example a hollow sphere.

The layer of porous material may be formed from any suitable porous material that is transparent at the wavelength being used for analysis. For example, the porous layer may be made from a sol-gel coating, a surfactant-templated material, a microparticulate coating, a layer of liquid crystal or the like.

The entire microresonator may also be made from a porous material, for example the porous glass Vycor™ available from Corning Inc., NY.

In addition, the porous layer may be doped with an optically active material. For example, the material of the porous layer may be doped with an optically excitable species, such as a rare earth ion, that produces optical gain. Thus, the light propagating within the microresonator may be used to pump the optically excitable species so as to obtain gain and/or laser oscillation at a wavelength amplifiable by the optically excitable species. The microresonator may oscillate at the wavelength amplifiable by the optically excitable species. Thus, the microresonator may be used to sense an analyte using a wavelength of light different from that coupled into the microresonator from the waveguide.

It will be appreciated that different types of optically active material may be introduced to the surface of the microresonator to interact with the light propagating within the WGM(s) of the microresonator. The interaction may, for example, include the absorption of light, the emission of light, or some other type of interaction. For example, an organic dye may be introduced to the surface of the microresonator, where the light propagating within the microresonator causes the dye to fluoresce. This may even lead to oscillation on a WGM at a wavelength of light amplified by the material introduced to the microresonator surface.

EXAMPLE 1

Porous Layer

A sol-gel approach is used in which pore forming agents such as surfactants are included for forming a porous layer over a core. This permits control of the pore sizes that can provide some size discrimination, for example, unimodal pores with a diameter in the range of about 2 to about 50 nm diameter, with diameter control <10%. When Stober spheres are used, the diameter range is from about 2 nm to 1000 nm or more.

A simple system involves combining tetraethoxysilane, nonionic surfactant, acid, water, and ethanol to form a coating solution. This solution can be applied to the core spheres by dipping or spraying. The surfactant can be removed if desired by liquid extraction or heating. The walls of the pores can be functionalized via silane coupling agents.

EXAMPLE 2

Porous Layer

Surfactant-templated silica films were dip-coated onto microsphere resonators and onto silicon substrates. The resonators and the silicon substrates were calcined at 400° C. for 15 minutes to remove the surfactant and leave nanometer diameter unimodal pores. Porosities of the films range from ~25 to ~50 volume percent, and refractive indices range from 1.21-1.34.

In this example, there are, by design, two sets of four samples (eight conditions). One set has film thicknesses that range from 40-55 nm; the second set has film thicknesses that range from 230-280 nm. Silica concentration in the coating solution is the key factor used to control thickness. Each set of four samples has two samples with small (~3 nm) and two samples with large (~10 nm) pore diameters. Surfactant formula weight is used to control pore diameter. Note that the pore diameters in both sets are much smaller than the wavelength of the probe light (>400 nm). It is anticipated that these porous coatings help to increase the sensitivity of resonator biosensors through increased surface loading of analytes. The coatings presented in this example are silica-based, although, in principle can be metal oxide-, metal sulfide-, metal-, or polymer-based.

A three-factor, two-level full-factorial designed experiment (eight conditions) was employed to examine the effect of the factors listed in Table I on coating thickness, coating porosity, shrinkage upon heating, refractive index, and pore diameter. Eight resonators (one with each condition) and 16 silicon substrates (two each with each condition) were coated with the surfactant-templated silica films. Each of the microspheres and one of the coated silicon substrates for each condition were calcined (see below for details). The as-made and calcined films on silicon substrates were characterized extensively by ellipsometry. It is assumed that the calcined films on the silicon substrates are a reasonable approximation of the calcined films on the resonators.

TABLE I

DOE Factors and Levels

| Factors | − | + |
| --- | --- | --- |
| Surfactant type (FW g/mol) | CTAB (365) | P123 (5150) |
| Surfactant/Silica ratio (V/V) | 1.8 | 3.5 |
| Relative Silica Concentration[1] | 0.19 | 1 |

[1]Based on ~0.62 M acid-adjusted-TEOS plus ethanol concentration for the + condition The first step in the preparation of coated resonators (and silicon substrates), was to synthesize a 2.16 M tetraethoxysilane-based solution. From this solution the eight coating solutions were prepared by adding the appropriate amounts of surfactant and ethanol solvent, as shown in Table II.

A 2.16 M silica sol stock solution was prepared by combination in a 9 L flask of 892 mL absolute ethanol (Aaper Alcohol and Chemical Company, Shelbyville, Ky.), 892 mL tetraethoxysilane (Alfa Aesar, Ward Hill, Mass.), 71.97 mL deionized water (18 MΩ), and 0.0210 mL concentrated HCL (JT Baker, Phillipsburg, N.J.; 29% aqueous). The solution was stirred with an overhead air-driven stirrer and heated on a programmable hot plate (with temperature probe) for 90 minutes at 60° C. After the solution cooled it was stored at 0° C. in polypropylene bottles.

To prepare the acid-adjusted TEOS solution referred to in Table II, 34.48 mL of the 2.16 M TEOS stock solution from the above paragraph, 4.14 mL 0.07 N HCl, and 1.38 mL deionized water (18 MΩ) were combined in a 60 mL polypropylene bottle.

The formulations presented in Table II were used to prepare the 8 coating solutions. The prescribed amount of acid-adjusted TEOS solution was transferred to a 60 mL polypropylene bottle with a micropipette. The surfactant and ethanol were added to the bottle and the contents were shaken vigorously until a clear homogeneous solution formed. Surfactants were Pluronic P123 ($EO_{20}PO_{70}EO_{20}$) (BASF, Mount Olive, N.J.) and cetyltrimethylammonium bromide ($CH_3C_{15}H_{30}N(CH_3)_3Br$ or CTAB; Aldrich, Milwaukee, Wis.).

TABLE II

DOE Run Order and Formulations

| Sample | Notation | StdOrder | RunOrder | Surfactant | Acid-adjusted TEOS soln (mL) | Surfactant (g) | Ethanol (mL) |
| --- | --- | --- | --- | --- | --- | --- | --- |
| 1 | −++ | 7 | 1 | CTAB | 6.67 | 1.18 | 13.33 |
| 2 | −−+ | 5 | 2 | CTAB | 6.67 | 0.59 | 13.33 |
| 3 | +−− | 2 | 3 | P123 | 1.25 | 0.12 | 18.75 |
| 4 | −−− | 1 | 4 | CTAB | 1.25 | 0.11 | 18.75 |
| 5 | +++ | 8 | 5 | P123 | 6.67 | 1.23 | 13.33 |
| 6 | −+− | 3 | 6 | CTAB | 1.25 | 0.22 | 18.75 |
| 7 | +−+ | 6 | 7 | P123 | 6.67 | 0.61 | 13.33 |
| 8 | ++− | 4 | 8 | P123 | 1.25 | 0.23 | 18.75 |

Note:
the "notation" column refers to the factors in Table I in the order they appear, i.e. surfactant type, surfactant/silica ratio, reactant concentration.

Each coating solution listed in Table II was transferred to a 20 mL scintillation vial. Silicon wafers <100> cut, p-type, B-doped (3" from Silicon Sense, Nashua, N.H.) were cut into ~1 cm×2 cm sections. The wafers were cleaned by sonicating in a LIQUINOX/deionized water solution for 2 minutes. The substrates were then rinsed with deionized water for 2 minutes and rinsed with ethanol prior to coating.

Each vial was placed successively in a dip-coating chamber. Two Si wafers and one microsphere were coated in turn with each solution. The wafers and sphere were held vertical. The immersion and withdrawal speeds into and out of the coating solution were 0.5 cm/s. The coatings were allowed to dry in air.

After three days, one wafer of each sample type and each coated resonator was placed into a 400° C. furnace and calcined for 15 minutes. The time to wait before calcining the samples need not be as long as this, and may be as short as a few hours.

After the wafer samples had cooled, ellipsometry was performed on the calcined and as-made films. Data (psi and delta) were measured on the films on silicon wafers at 50° and 70° with a Gaertner L116A ellipsometer (Skokie, Ill.) that employs 632.8 nm light from a monochromatic HeNe laser. At least three spots were measured for each sample. Reported values are averages. Values for the thickness, t, and the refractive index, n, of the single layer films were determined by the software provided with the ellipsometer. Parameters for the substrate were index Ns=3.850; absorption coefficient Ks=−0.020; wavelength 632.8 nm. Results are reported in Tables III and IV and in FIGS. 5 and 6.

TABLE III

Thicknesses and Refractive Indices of As-made
(Uncalcined) Samples on Silicon Wafers

| Sample | Notation | AVE t (Å) | SD t (Å) | Percent error (SD/AVE) | AVE n | SD n | Percent Error (SD/AVE) |
|---|---|---|---|---|---|---|---|
| 1 | −++ | 4256 | 265 | 6.23 | 1.479 | 0.001 | 0.08 |
| 2 | −−+ | 5826 | 173 | 2.99 | 1.486 | 0.009 | 0.60 |
| 3 | +−− | 675 | 7 | 0.99 | 1.456 | 0.001 | 0.03 |
| 4 | −−− | 614 | 11 | 1.74 | 1.449 | 0.003 | 0.20 |
| 5 | +++ | 3628 | 244 | 6.71 | 1.456 | 0.001 | 1.93 |
| 6 | −+− | N/A | N/A | N/A | N/A | N/A | N/A |
| 7 | +−+ | 4348 | 143 | 3.29 | 1.463 | 0.001 | 0.03 |
| 8 | ++− | 1037 | 30 | 2.90 | 1.452 | 0.020 | 1.38 |

N/A - film was too hazy to get data.

TABLE IV

Thicknesses and Refractive Indices of Calcined Samples on Silicon Wafers

| Sample | Notation | AVE t (Å) | SD t (Å) | % error (SD/AVE) | AVE n | SD n | % error (SD/AVE) | porosity (%) | Shrinkage (%) |
|---|---|---|---|---|---|---|---|---|---|
| 1 | −++ | 2348 | 13 | 0.6 | 1.318 | 0.002 | 0.13 | 28 | 45 |
| 2 | −−+ | 2788 | 52 | 1.9 | 1.232 | 0.008 | 0.66 | 46 | 52 |
| 3 | +−− | 383 | 13 | 3.3 | 1.338 | 0.008 | 0.60 | 24 | 43 |
| 4 | −−− | 453 | 12 | 2.6 | 1.276 | 0.001 | 0.09 | 37 | 26 |
| 5 | +++ | 2628 | 146 | 5.6 | 1.320 | 0.020 | 1.51 | 28 | 28 |
| 6 | −+− | 533 | 18 | 3.4 | 1.218 | 0.014 | 1.16 | 49 | |
| 7 | +−+ | 2815 | 15 | 0.5 | 1.317 | 0.001 | 0.09 | 28 | 35 |
| 8 | ++− | 415 | 15 | 3.5 | 1.314 | 0.007 | 0.53 | 29 | 60 |

Porosity was calculated from the Lorentz-Lorenz relationship:

$$P = 100 * (1 - [((n_{silica}^2 - 1)/(n_{silica}^2 + 2))/((n_{sample}^2 - 1)/(n_{sample}^2 + 2))])$$

The refractive index of silica was assumed to be 1.460. Shrinkage was calculated from the following equation:

$$S = 100 * [1 - t_{calcined}/t_{as\text{-}made}]$$

Figure 5:
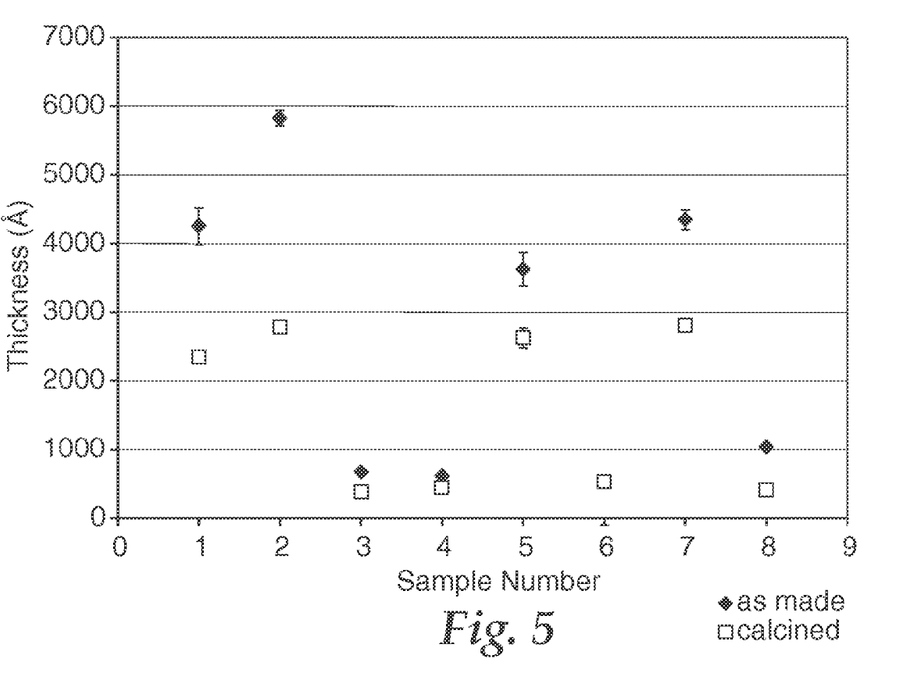
FIG. 5 presents a graph showing experimentally obtained porous film thickness for various samples fabricated according to the present invention.
Figure 6:
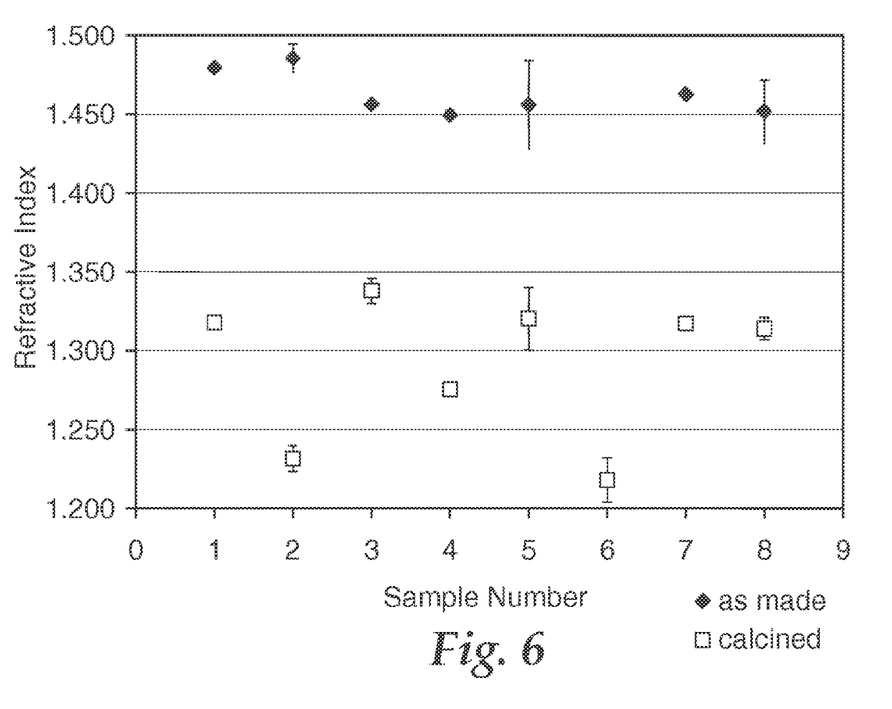
FIG. 6 presents a graph showing experimentally obtained values of refractive index for various samples fabricated according to the present invention.

FIG. 5 shows a graph with film thickness values, t, for as-made and calcined samples as measured by ellipsometry. FIG. 6 shows a graph of refractive index values, n, for as-made and calcined samples on silicon wafers, as measured by ellipsometry.

For the data on calcined samples, a main effects plot, interactions plot, cube plot, and effects analysis (Pareto) were produced for the outputs: thickness, refractive index, shrinkage, and porosity. The results are summarized in Table V.

TABLE V

Summary of Main Effects

| Output | Important x's | Output is max when factor is: |
|---|---|---|
| Thickness | Silica concentration | Greater |
| Refractive index | None (surf type) | (smaller) |
| Shrinkage | Surf type/conc interaction | Large surf/low conc and small surf/high conc |
| Porosity | None (surf type) | (smaller) |

Note:
an alpha value of 0.1 was used to define significance; effect of surfactant type on index was examined with t-test; p = 0.079. Note that the shrinkage for sample 6 could not be calculated owing to the inability to measure refractive index of the as-made film. Parenthesis indicates not statistically significant in at alpha = 0.1 in the Effects Analysis.

There is a strong correlation between coating thickness and silica concentration—as expected. There is no statistically significant correlation of coating porosity or refractive index with any of the x's. There is correlation between shrinkage and surfactant type/concentration. Specifically, the largest values of shrinkage tend to occur with large surfactants and low reactant concentrations or small surfactants and high reactant concentrations.

EXAMPLE 3

Experimental Results Using Porous Microresonators

Experiments were carried out to determine the effective Q-factors of microresonators fabricated according to the procedure outlined in Example 2. The experimental arrangement was similar to that shown in FIG. 1A. In each experiment, a fiber 108 was placed in contact with the microresonator 110 and both were immersed in water. A tunable diode laser (Velocity 6304 from New Focus) was used as light source 102 with the wavelength centered at around 630 nm. The wavelength of the light emitted by the laser was tuned by varying the voltage that drives a piezo-actuator inside the laser. When the wavelength was on-resonance with one or more of the whispering gallery modes 112 of the microresonator, the amount of laser power coupled into the microresonator was increased, leading to a power drop at the detector 106.

Figure 7:
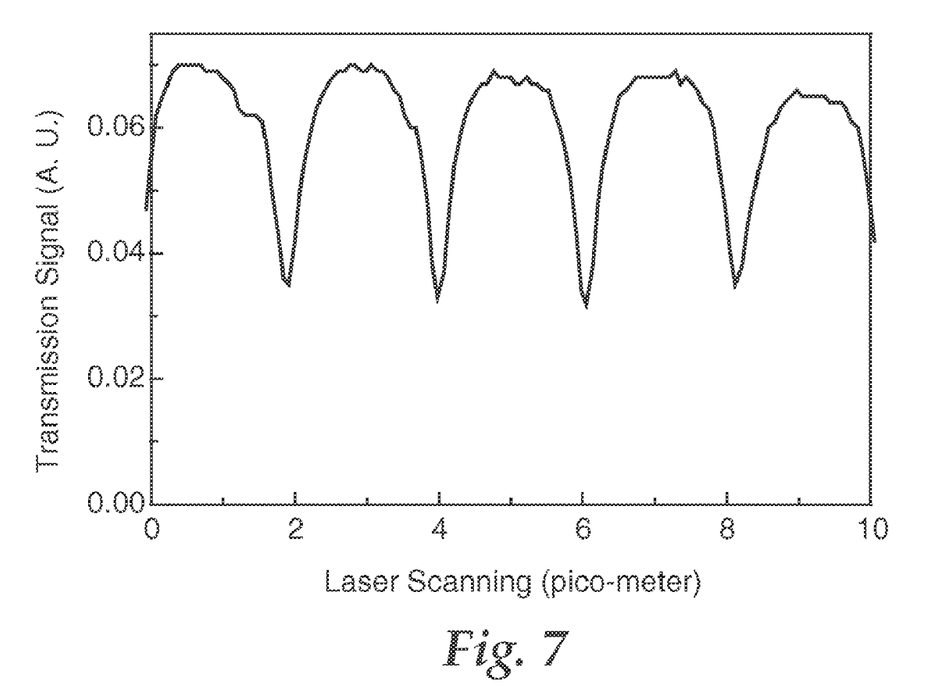
FIGS. 7 and 8 present graphs showing experimentally obtained resonance plots for different embodiments of microresonator fabricated in accordance with principles of the present invention.
Figure 8:
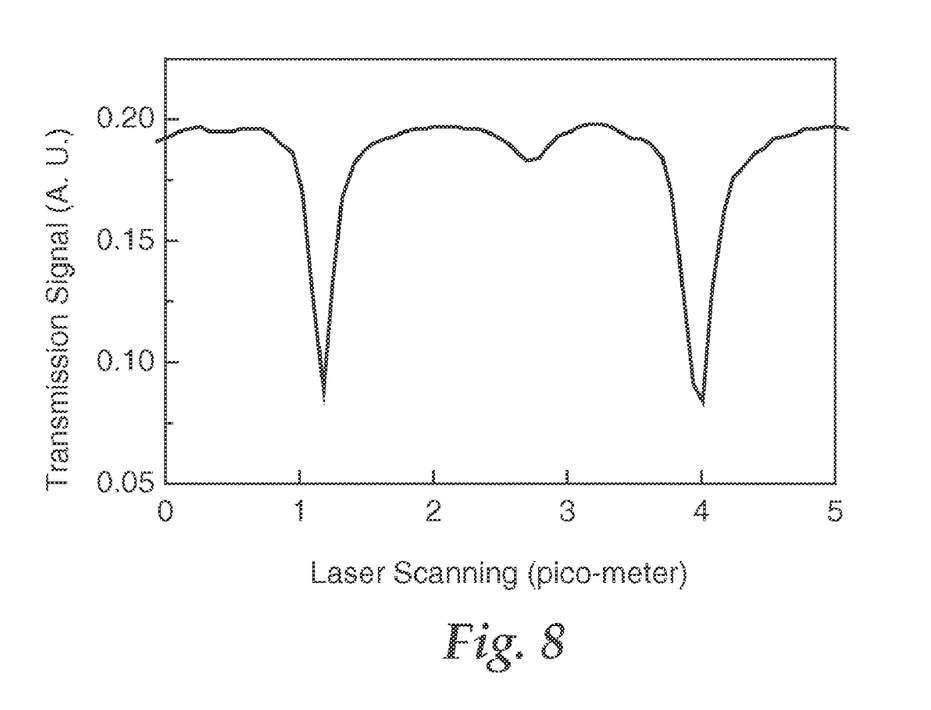

FIG. 7 shows the detected signal at the detector as a function of laser tuning, where the microresonator was formed according to sample number 6, in Table II. The Q-factor of the microresonator was estimated from these results to be approximately $1.4 \times 10^6$. FIG. 8 shows the detected signal at the detector as a function of laser tuning, where the microresonator was formed according to sample number 7, in Table II. The Q-factor of the microresonator was estimated from these results to be approximately $2.8 \times 10^6$.

These two results confirm that high Q-factors can still be achieved in microresonators that have porous outer layers.

As noted above, the present invention is applicable to microresonators, and is believed to be particularly useful where microresonators are used in sensing applications. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A microresonator system comprising a microresonator having at least a porous surface region, an excited optical mode of the microresonator decaying within a core of the microresonator.

2. A system as recited in claim 1, wherein the excited optical mode is a whispering gallery mode.

3. A system as recited in claim 1 further comprising a light source optically coupled to the microresonator.

4. A system as recited in claim 1 further comprising a first waveguide for coupling light into the microresonator.

5. A system as recited in claim 1, wherein the microresonator is formed entirely from porous material.

6. A system as recited in claim 1, wherein the microresonator includes a porous outer layer disposed over the core.

7. A system as recited in claim 6, wherein the core is a non-porous core.

8. A system as recited in claim 1 further comprising a detector receiving light from the microresonator.

9. A system as recited in claim 8 further comprising a second waveguide coupling light between the microresonator and the detector.

10. A system as recited in claim 1, wherein the porous surface region is modified to attract an analyte.

11. A system as recited in claim 1, wherein the porous surface region of the microresonator is provided with one of an antigen and an associated antibody.

12. A system as recited in claim 1, wherein the porous surface region has a thickness less than a wavelength of the excited optical mode.

13. A system as recited in claim 1, wherein the porous surface region has a thickness less than one tenth of the wavelength of the excited optical mode.

14. A system as recited in claim 1, wherein the microresonator is substantially spherical.

15. A system as recited in claim 1, wherein the microresonator is substantially planar.

* * * * *

UNITED STATES PATENT AND TRADEMARK OFFICE
CERTIFICATE OF CORRECTION

PATENT NO. : 7,595,890 B2  Page 1 of 1
APPLICATION NO. : 11/837604
DATED : September 29, 2009
INVENTOR(S) : Xudong Fan

It is certified that error appears in the above-identified patent and that said Letters Patent is hereby corrected as shown below:

Title Page 3

Column 2; Other Publications; Line 11, Delete "Microbioology" and insert
-- Microbiology --, therefor.

Signed and Sealed this

First Day of June, 2010

David J. Kappos
*Director of the United States Patent and Trademark Office*